US00PP29297P2

(12) United States Plant Patent
Kerley

(10) Patent No.: US PP29,297 P2
(45) Date of Patent: May 15, 2018

(54) ***BEGONIA* PLANT NAMED 'KERBESPIROS'**

(50) Latin Name: *Begonia tuberhybrida*
Varietal Denomination: KERBESPIROS

(71) Applicant: Timothy Kerley, Over (GB)

(72) Inventor: Timothy Kerley, Over (GB)

( * ) Notice: Subject to any disclaimer, the term of this patent is extended or adjusted under 35 U.S.C. 154(b) by 0 days. days.

(21) Appl. No.: 15/530,704

(22) Filed: Feb. 17, 2017

(51) Int. Cl.
*A01H 5/02* (2018.01)

(52) U.S. Cl.
USPC ..... Plt./344

(58) Field of Classification Search
USPC ..... Plt./344
See application file for complete search history.

*Primary Examiner* — Annette H Para
(74) *Attorney, Agent, or Firm* — Cassandra Bright

(57) ABSTRACT

A new and distinct *Begonia tuberhybrida* cultivar named 'KERBESPIROS' is disclosed, characterized by rose pink colored, strongly fragrant flowers. Plants are semi-upright, free-branching with excellent weather tolerance. The new variety is a *Begonia*, and is normally used as an ornamental garden or container plant.

2 Drawing Sheets

Latin name of the genus and species: *Begonia tuberhybrida.*

Variety denomination: 'KERBESPIROS'.

BACKGROUND OF THE INVENTION

The new cultivar is the product of a planned breeding program. The new variety originated as the result of a crossing performed during September 2015 of *Begonia* 'Fragrant Blush' (unpatented) with the pollen parent, a proprietary variety of *Begonia tuberhybrida* referred to as '05-355-19'. The selection of the new variety was made in July 2016, by the inventor at a research greenhouse located in Cambridge, UK.

Asexual reproduction of the new cultivar 'KERBESPIROS' was first performed at a research greenhouse located in Cambridge, UK by terminal vegetative cuttings during July 2016. 'KERBESPIROS' has since produced multiple generations by vegetative cuttings and has shown that the unique features of this cultivar are stable and reproduced true to type.

SUMMARY OF THE INVENTION

The cultivar 'KERBESPIROS' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'KERBESPIROS'. These characteristics in combination distinguish 'KERBESPIROS' as a new and distinct *Begonia tuberhybrida* cultivar:

1. Semi-trailing plant habit.
2. Strongly fragrant flowers.
3. Rose pink flower color.
4. Free branching.
5. Medium flower size.

6. Excellent weather tolerance
7. Suitability for pot sizes 12 cm and larger.

PARENT COMPARISON

Plants of the new cultivar 'KERBESPIROS' are similar to plants of the seed parent variety in most horticultural characteristics. However, plants of the new cultivar 'KERBESPIROS' differ in the following:

1. Flowers of the new variety are rose pink, flowers of the seed parent are cream with pink blush.
2. Plants of the new variety have a semi-trailing habit, plants of the seed parent are more upright.
3. Stems of the new variety are smaller in diameter than the seed parent.
4. Plants of the new variety branch more abundantly than the seed parent.

Plants of the new cultivar 'KERBESPIROS' are similar to plants of the pollen parent variety in most horticultural characteristics. However, plants of the new cultivar 'KERBESPIROS' differ in the following:

1. Flowers of the new variety are rose pink, flowers of the pollen parent are orange.
2. Flowers of the new variety are strongly fragrant, flowers of the pollen parent are unscented.

COMMERCIAL COMPARISON

Plants of the new cultivar 'KERBESPIROS' are similar to plants of the commercial variety, *Begonia* 'Fragrant Falls Apricot Improved', in most horticultural characteristics. However, plants of the new cultivar 'KERBESPIROS' differ in the following:

1. Flowers of the new variety are rose pink, flowers of this comparator are apricot colored.
2. Flowers of the new variety are smaller than those of this comparator.
3. Plants of the new variety are significantly more free branching than this comparator.
4. Plants of the new variety are semi-upright, plants of this comparator are upright, then lodging over with age.

Plants of the new cultivar 'KERBESPIROS' are similar to plants of the commercial variety, *Begonia* '77WL Peach', U.S. Plant Pat. No. 12,786, in most horticultural characteristics. However, plants of the new cultivar 'KERBESPIROS' differ in the following:

1. Flowers of the new variety are rose pink, flowers of this comparator are apricot colored.
2. Flowers of the new variety are smaller than those of this comparator.
3. Plants of the new variety are significantly more free branching than this comparator.
4. Plants of the new variety are semi-upright, plants of this comparator are upright, then lodging over with age.

BRIEF DESCRIPTION OF THE PHOTOGRAPH

The present invention of a new and distinct variety of Calendula is shown in the accompanying photographs, the colors being as nearly true as possible with color photographs of this type.

DETAILED BOTANICAL DESCRIPTION

Figure 1:
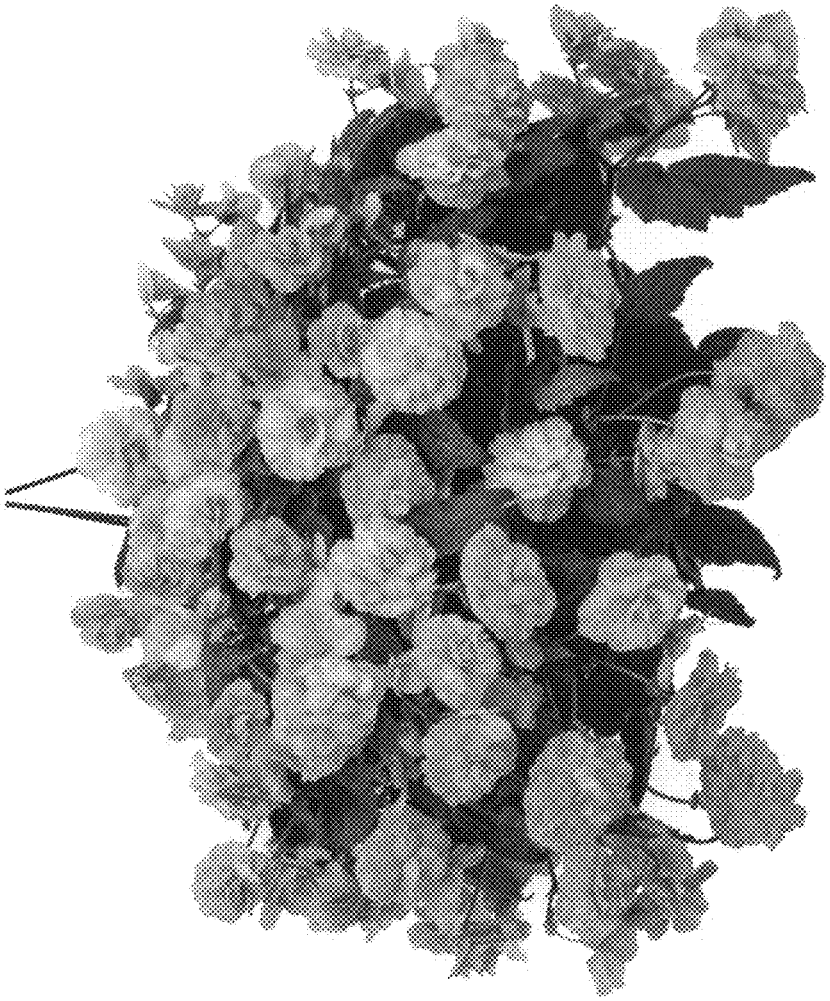
FIG. 1 illustrates a plant of approximately 5 months in a 20 cm pot
Figure 2:
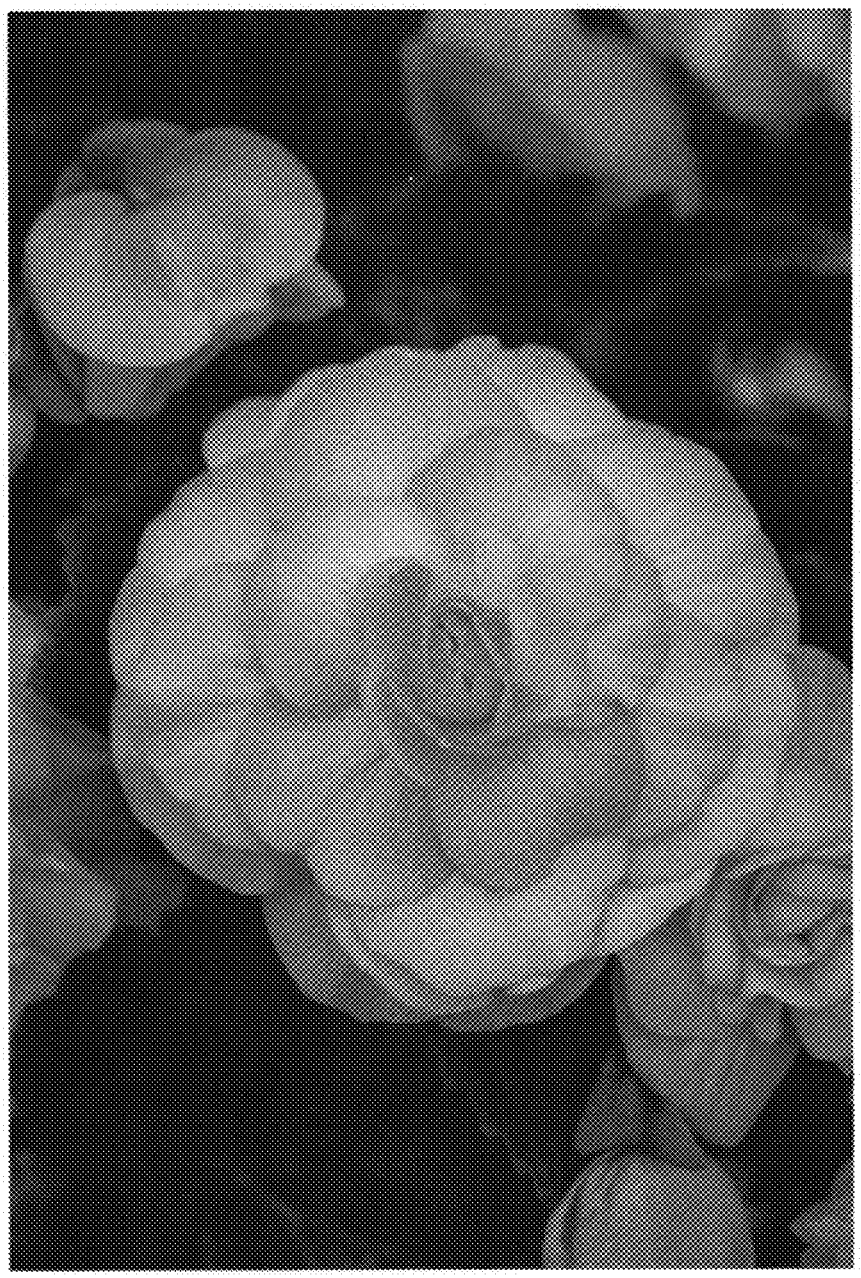
FIG. 2 illustrates a close up of the inflorescence.

In the following description, color references are made to The Royal Horticultural Society Colour Chart 2001 except where general terms of ordinary dictionary significance are used. The following observations and measurements describe 'KERBESPIROS' plants grown in a commercial controlled greenhouse in Cambridge, United Kingdom. Measurements and numerical values represent averages of typical plant types.

Botanical classification: *Begonia tuberhybrida* 'KERBESPIROS'.

Age of plant described: Approximately 15 weeks.

Container of plant described: Window box.

PROPAGATION

Type of propagation typically used: Vegetative tip cuttings.

Time to develop roots: About 10 days at approximately 21° C.

Time to develop a rooted liner: About 21 days at approximately 21° C.

Root description: Fibrous, fine, well branched. White and tan, not accurately measured with The R.H.S. chart.

PLANT

Growth habit: Semi-upright.

Height: 17 cm.

Plant spread: 26 cm.

Growth rate: Moderate.

Branching characteristics: Well branched.

Characteristics of primary lateral branches:

- *Form*.—Round in cross section.
- *Length*.—Approximately 17 cm.
- *Diameter*.—Approximately 0.8 cm.
- *Color*.—Near RHS Greyed-Red 178B with some Grey-Brown 199B.
- *Texture*.—Fleshy with small white hairs.
- *Strength*.—Moderately strong and flexible.

Internode length: Average 1.9 cm.

Foliage:

- *Arrangement*.—Alternate.
- *Quantity*.—Approximately 7 per primary lateral branch.
- *Average length*.—Approximately 11.0 cm.
- *Average width*.—Approximately 6.5 cm.
- *Shape of blade*.—Cordate.
- *Apex*.—Acute.
- *Base*.—Cordate.
- *Margin*.—Double serrate.
- *Texture of top surface*.—Densely pubescent, hairs approximately 2 mm.
- *Texture of bottom surface*.—Densely pubescent, hairs approximately 2 mm.
- *Aspect*.—Strong upward curve to overall leaf, margins slightly curled under.
- *Color*.—Young foliage upper side: Darker than Yellow-Green 148A. Young foliage under side: Near RHS Yellow-Green 148A and 148B. Mature foliage upper side: Near RHS Yellow-Green 147A. Mature foliage under side: Near RHS Yellow-Green 148B with 183D at the outer edge.
- *Venation*.—Type: Palmate. Venation color upper side: Near RHS Yellow-Green 148A. Venation color under side: Between RHS Yellow-Green 148A and 148B.
- *Petiole*.—Length: Approximately 4 cm. Diameter: Approximately 0.4 cm. Color: Near RHS Greyed-Orange 174A. Texture: Pubescent.
- *Stipule description*.—Usually 1 per leaf, occasionally 2. Length: Approximately 0.7 cm. Diameter: Approximately 0.5 cm. Color: Near RHS Yellow-Green 145B. Texture: Glabrous.

FLOWER

Flowering season: May to September in Cambridge, UK.

Flower type and habit: Double male flowers, single female flowers.

Persistent or self-cleaning: Self-Cleaning.

Bud:

- *Shape*.—Orbicular.
- *Length*.—Approximately 1.6 cm.
- *Diameter*.—Approximately 2.0 cm.
- *Color*.—Near Greyed-Orange 174D with Green-White 157A base.

Flower size:

- *Male*.—Diameter: Approximately 6.5 cm. Depth: Approximately 2.5 cm.
- *Female*.—Diameter: Approximately 5.5 cm. Depth: Approximately 1.0 cm.

Tepals:

- *Quantity*.—Male: Approximately 45 to 50. Female: 5.
- *Arrangement*.—Rosette.
- *Length*.—Longest, approximately 3.4 cm.
- *Width*.—Approximately 4.2 cm.
- *Shape*.—Obovate.
- *Apex*.—Obtuse.
- *Base*.—Rounded.
- *Margin*.—Entire.
- *Texture, upper and lower surfaces*.—Matte.

*Color*.—Male Outer Tepals — When opening, upper surface: Between Red 50B and 50C. Apex 50A. Base Yellow 3B. When opening, lower surface: Between Red 50C and 50D. Base Yellow 3A. Male Inner Tepals When opening, upper surface: Between Red 50C and 50D. Base Yellow 3D Apex 50B. When opening, lower surface: Between Red 50C and 50D. Base Yellow 3D Apex 50B Male Outer Tepals — Fully opened, upper surface: Between Red 50A and 50B. Base Orange 26A. Fully opened, lower surface: Near RHS Red 50A. Male Inner Tepals — Fully opened, upper surface: Between Red 50C and 50D. Base Yellow-Orange 17C. Fully opened, lower surface: Between Red 50C and 50D. Base Yellow-Orange 17B.

*Color*.—Female Flower Tepals — Immature, upper surface: Between Red 49A and 50B. Base Yellow 3C. Immature, lower surface.: Between Red 49A and 51B. Base Green-Yellow 1C. Fully opened, upper surface: Between Red 49A and 56A. Base Yellow 13A. Fully opened, lower surface: Near Red 49A with a hint of 54A. Base Yellow 13A.

Flower bracts:

*Quantity per flower*.—2, opposite.
*Shape*.—Ovate.
*Length*.—Approximately 1.1 cm.
*Diameter*.—Approximately 0.6 cm.
*Apex*.—Obtuse.
*Margin*.—Entire.
*Texture*.—Glabrous.
*Color*.—Near RHS Yellow-Green 145A.

Peduncles:

*Length*.—Average 8.1 cm.
*Diameter*.—Approximately 0.2 cm.
*Angle*.—About 15° to the lateral branch.
*Strength*.—Moderate, flexible.
*Texture*.—Glabrous, shiny.
*Color*.—Near Yellow-Green 152A with blush Greyed-Red 178A.

Pedicels:

*Length*.—Average 3.3 cm.
*Diameter*.—Approximately 0.2 cm.
*Angle*.—About 15° to the lateral branch.
*Strength*.—Moderate, flexible.
*Texture*.—Glabrous, shiny.
*Color*.—Mature near Yellow-Green 146C with blush Greyed-Red 178B. Immature Yellow-Green 146B with Red 39A.

Fragrance: Strongly scented.

REPRODUCTIVE ORGANS

Androecium: Not observed.

Pistil: Highly reduced, minute multi-lobed stigma present.

OTHER CHARACTERISTICS

Seeds and fruits: Not observed to date.

Disease/pest resistance: Neither resistance nor susceptibility to diseases or pests of *Begonia* has been observed in this variety.

Temperature tolerance: The new variety tolerates temperatures from approximately 5° to 35° C.

Other features: Excellent weather tolerance.

What is claimed is:

1. A new and distinct cultivar of *Begonia* plant named 'KERBESPIROS' as herein illustrated and described.

* * * * *